United States Patent
Ellis

(10) Patent No.: US 7,368,599 B2
(45) Date of Patent: May 6, 2008

(54) ETHANE OXIDATION CATALYST AND PROCESS UTILISING THE CATALYST

(75) Inventor: Brian Ellis, Lower Sunbury (GB)

(73) Assignee: BP Chemicals Limited, Middlesex (GB)

( * ) Notice: Subject to any disclaimer, the term of this patent is extended or adjusted under 35 U.S.C. 154(b) by 222 days.

(21) Appl. No.: 10/491,287

(22) PCT Filed: Sep. 4, 2002

(86) PCT No.: PCT/GB02/04018

§ 371 (c)(1), (2), (4) Date: Mar. 31, 2004

(87) PCT Pub. No.: WO03/033138

PCT Pub. Date: Apr. 24, 2003

(65) Prior Publication Data

US 2004/0249204 A1    Dec. 9, 2004

(30) Foreign Application Priority Data

Oct. 16, 2001 (GB) ................. 0124835.0
Aug. 13, 2002 (GB) ................. 0218870.4

(51) Int. Cl.
*C07C 51/16* (2006.01)

(52) U.S. Cl. ..................... 562/548; 562/549

(58) Field of Classification Search ............... 562/512, 562/523, 544, 549, 607; 502/305, 308, 310, 502/311, 312, 313, 314, 316, 322
See application file for complete search history.

(56) References Cited

U.S. PATENT DOCUMENTS 6,333,444 B1 * 12/2001 Ellis et al. ................. 585/658

FOREIGN PATENT DOCUMENTS

| EP | 1 043 064 A2 | 10/2000 |
|---|---|---|
| EP | 1043064 | * 10/2000 |
| EP | 1 192 987 A1 | 4/2002 |
| WO | WO 99/51339 | 10/1999 |

* cited by examiner

*Primary Examiner*—Karl Puttlitz
(74) *Attorney, Agent, or Firm*—Nixon & Vanderhye

(57) ABSTRACT

A catalyst composition and its use for the selective oxidation of ethane to acetic acid and/or for the selective oxidation of ethylene to acetic acid. The composition includes in combination with oxygen the elements molybdenum, vanadium, niobium, gold in the absence of palladium according to the empirical formula $Mo_a W_b Au_c V_d Nb_e Z_f$, wherein Z is one or more elements selected from B, Al, Ga, In, Ge, Sn, Pb, Sb, Cu, Pt, Ag, Fe and Re, and a, b, c, d, e and f represent the gram atom ratios of the elements such that: $0 < a \leq 1$; $0 \leq b < 1$ and $a+b=1$; $10^{-5} \phi c \leq 0.02$; $0 < d \leq 2$; $0 < e \leq 1$; and $0.0001 \leq f \leq 0.05$.

13 Claims, No Drawings

ETHANE OXIDATION CATALYST AND PROCESS UTILISING THE CATALYST

This application is the U.S. National Phase of International Application PCT/GB02/04018, filed 4 Sep. 2002, which designated the U.S.

The present invention relates to a catalyst for the selective oxidation of ethane to acetic acid and/or for the selective oxidation of ethylene to acetic acid, and to a process for the production of acetic acid utilising the aforesaid catalyst.

Catalysts comprising molybdenum, vanadium and niobium in combination with oxygen for use in processes for the production of acetic acid by the oxidation of ethane and ethylene are known in the art from, for example, U.S. Pat. No. 4,250,346, EP-A-1043064, WO 99/20592 and DE 196 30 832.

U.S. Pat. No. 4,250,346 discloses the oxidative dehydrogenation of ethane to ethylene in a gas phase reaction at relatively high levels of conversion, selectivity and productivity to ethylene at a temperature of less than about 550° C. using as a catalyst a composition comprising the elements molybdenum, X and Y in the ratio $Mo_aX_bY_c$ wherein X is Cr, Mn, Nb, Ta, Ti, V and/or W, and preferably Mn, Nb, V and/or W; Y is Bi, Ce, Co, Cu, Fe, K, Mg, Ni, P, Pb, Sb, Si, Sn, Tl and/or U, and preferably Sb, Ce and/or U, a is 1, b is 0.05 to 1.0 and c is 0 to 2, and preferably 0.05 to 1.0, with the proviso that the total value of c for Co, Ni and/or Fe is less than 0.5.

WO 99/20592 relates to a method of selectively producing acetic acid from ethane, ethylene or mixtures thereof and oxygen at high temperature in the presence of a catalyst having the formula $Mo_aPd_bX_cY_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

The catalysts of both WO 99/20592 and DE 19630832 require the presence of palladium.

EP-A-1043064 discloses a catalyst composition for the oxidation of ethane to ethylene and/or acetic acid and/or for the oxidation of ethylene to acetic acid which comprises in combination with oxygen the elements molybdenum, vanadium, niobium and gold in the absence of palladium according to the empirical formula:

$$Mo_aW_bAu_cV_dNb_eY_f \quad (I)$$

wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te, La and Pd; a, b, c, d, e and f represent the gram atom ratios of the elements such that: $0<a\leq 1$; $0\leq b<1$ and $a+b=1$; $10^{-5}<c\leq 0.02$; $0<d\leq 2$; $0<e\leq 1$; and $0\leq f\leq 2$.

There remains a need to develop a catalyst for the oxidation of ethane and/or ethylene to acetic acid and a process for the production of acetic acid using said catalyst and wherein the catalyst enables a high selectivity to acetic acid to be achieved.

Surprisingly, it has now been found that it is possible by using a catalyst that contains, in combination with oxygen, the elements molybdenum, vanadium, niobium and gold and one or more elements selected from the group consisting of boron, aluminum, gallium, indium, germanium, tin, lead antimony, copper, platinum, silver, iron and rhenium, in the absence of palladium, to oxidise ethane and/or ethylene to acetic acid with a high selectivity to acetic acid. Furthermore, it has been found possible using the catalyst of the present invention, to achieve a high selectivity to acetic acid with reduced, for example, little, if any, selectivity to ethylene.

Accordingly, the present invention provides a catalyst composition for the selective oxidation of ethane to acetic acid and/or for the selective oxidation of ethylene to acetic acid which composition comprises in combination with oxygen the elements molybdenum, vanadium, niobium, gold in the absence of palladium according to the empirical formula:

$$Mo_aW_bAu_cV_dNb_eZ_f \quad (I)$$

wherein Z is one or more elements selected from the group consisting of B, Al, Ga, In, Ge, Sn, Pb, Sb, Cu, Pt, Ag, Fe and Re; a, b, c, d, e and f represent the gram atom ratios of the elements such that:
$0<a\leq 1$; $0\leq b<1$ and $a+b=1$;
$10^{-5}<c\leq 0.02$;
$0<d\leq 2$;
$0<e\leq 1$; and
$0.0001\leq f\leq 0.05$
Catalyst embraced within the formula (I) include:
$Mo_aW_bAu_cV_dNb_eSn_f$
$Mo_aAu_cV_dNb_eSn_f$
Preferably, Z is Sn, Ag, Fe or Re, especially Sn.
Examples of suitable catalysts having the formula (I) include:
$Mo_{1.000}V_{0.423}Nb_{0.115}Au_{0.008}Ag_{0.008}Oy$,
$Mo_{1.000}V_{0.423}Nb_{0.115}Au_{0.008}Fe_{0.0156}Oy$,
$Mo_{1.000}V_{0.423}Nb_{0.115}Au_{0.008}Re_{0.008}Oy$,
$Mo_{1.00}V_{0.423}Nb_{0.115}Au_{0.0008}Sn_{0.0008}Oy$, and
$Mo_{1.00}V_{0.423}Nb_{0.117}Au_{0.0008}Sn_{0.0156}Oy$, wherein y is a number which satisfies the valencies of the elements in the composition for oxygen.
Preferably $0.01<a\leq 1$. Preferably, $0.1<d\leq 2$. Preferably, $0.01<e\leq 0.5$, for example, $0.05\leq e\leq 0.15$. Preferably, $0.0005\leq f\leq 0.02$.

An advantage of the catalyst compositions of the present invention is that they are highly selective in converting ethane and/or ethylene to acetic acid. Typically, using the catalyst compositions of the present invention, a selectivity to acetic acid of at least 50 mol %, preferably at least 60 mol %, such as at least 70 mol %, may be achieved.

In particular, using the catalyst compositions of the present invention, a high selectivity to acetic acid may be achieved in combination with a low, if any, selectivity to ethylene.

Typically, using the catalyst compositions of the present invention, the selectivity to ethylene is less than 25 mol %, preferably, less than 10 mol %, such as less than 5 mol %.

Preferably, using the catalyst compositions of the present invention, the selectivity to acetic acid is at least 60 mol %, such as at least 70 mol % and the selectivity to ethylene is less than 15 mol %, such as less than 10 mol %.

As used herein, selectivity refers to a percentage that reflects the amount of desired acetic acid product produced as compared to the total carbon in the products formed:

% selectivity=100*Moles of acetic acid produced/S wherein S=the molar acid-equivalent sum (carbon basis) of all carbon-containing products, excluding the alkane in the effluent The catalyst compositions may be prepared by any of the methods conventionally employed for the preparation of catalysts. Suitably the catalyst may be prepared from a solution of soluble compounds and/or complexes and/or compounds of each of the metals. The solution is preferably an aqueous system having a pH in the range from 1 to 12, preferably from 2 to 8, at a temperature of from 20° to 100° C.

Generally, a mixture of compounds containing the elements is prepared by dissolving sufficient quantities of soluble compounds and dispersing any insoluble compounds so as to provide a desired gram-atom ratio of the elements in the catalyst composition. The catalyst composition may then be prepared by removing the solvent from the mixture. The catalyst may be calcined by heating to a temperature of from 200 to 550° C., suitably in air or oxygen, for a period of from 1 minute to 24 hours. Preferably, the air or oxygen is slowly flowing.

The catalyst may be used unsupported or supported. Suitable supports include silica, alumina, zirconia, titania, silicon carbide and mixtures of two or more thereof.

Further details of a suitable method for preparing a catalyst composition may be found in, for example, EP-A-0166438.

The catalyst may be used in the form of a fixed or a fluidised bed.

In another embodiment the present invention provides a process for the selective production of acetic acid from a gaseous mixture comprising ethane and/or ethylene which process comprises contacting the gaseous mixture with a molecular oxygen-containing gas at elevated temperature in the presence of a catalyst composition as hereinbefore described.

Ethane is selectively oxidised to acetic acid and/or ethylene is selectively oxidised to acetic acid. Preferably, ethane and optionally ethylene is oxidised to a mixture comprising acetic acid which may be used with or without the addition or removal of acetic acid for the production of vinyl acetate by reaction with a molecular oxygen-containing a gas in an integrated process.

The feed gas comprises ethane and/or ethylene, preferably ethane.

Ethane and/or ethylene may be used in substantially pure form or admixed with one or more of nitrogen, methane, carbon dioxide and water in the form of steam, which may be present in major amounts, for example greater than 5 volume percent or one or more of hydrogen, carbon monoxide, $C_3/C_4$ alkenes and alkenes, which may be present in minor amounts, for example less than 5 volume percent.

The molecular oxygen-containing gas may be air or a gas richer or poorer in molecular oxygen than air, for example oxygen. A suitable gas may be, for example, oxygen diluted with a suitable diluent, for example nitrogen.

It is preferred to feed, in addition to ethane and/or ethylene and the molecular oxygen-containing gas, water (steam) because this can improve the selectivity to acetic acid.

The elevated temperature may suitably be in the range from 200 to 500° C., preferably from 200 to 400° C.

The pressure may suitably be atmospheric or superatmospheric, for example in the range from 1 to 50 bar, preferably from 1 to 30 bar.

The catalyst composition is preferably calcined before use in the process of the invention. Calcination may suitably be achieved by heating at a temperature suitably in the range from 250 to 500° C. in the presence of an oxygen-containing gas, for example air.

Operating conditions and other information applicable to the performance of the invention may be found in the aforesaid prior art, for example U.S. Pat. No. 4,250,346.

The process of the invention will now be further illustrated by reference to the following Examples.

CATALYST PREPARATION

Preparation of Catalyst A (Comparative)

A solution 'A' was prepared by dissolving 22.935 g of ammonium molybdate and 0.0357 g of ammonium gold chloride in 100 ml of distilled water at 70° C. with stirring. A solution 'B' was prepared by dissolving 6.434 g of ammonium vanadate in 150 ml of distilled water at 70° C. with stirring. A solution 'C' was prepared by dissolving 7.785 g of ammonium niobium oxalate in 100 ml of distilled water at 70° C. with stirring. Each of the solutions A, B and C was left for 15 minutes to allow maximum solubilisation of the components. Solution C was then added to solution B rapidly with stirring at 70° C. The mixed solution B/C was stirred for 15 minutes at 70° C. then added rapidly to solution A. The final mixed solution A/B/C was left to stir at 70° C. for a further 15 minutes, after which the solution was heated to boiling to facilitate evaporation of the water. Full evaporate of the reactant mixture was achieved in 1.5 hours, resulting in a dry paste. The beaker with the dried paste was then transferred to an oven for further drying at 120° C. for 2 hours. After drying, the catalyst precursor was ground to a fine powder and then sieved through a 0.2 mm mesh sieve. The resulting powdered catalyst cake was then calcined in static air in an oven at 400° C. for 4 hours. The nominal formula of the oxide catalyst obtained was:

$$Mo_{1.000}V_{0.423}Nb_{0.115}Au_{0.0008}O_y$$

This catalyst is not a catalyst according to the invention because it contains no element from the group consisting of B, Al, Ga, In, Ge, Sn, Pb, Sb, Cu, Pt, Ag, Fe and Re.

Preparation of Catalyst B

A catalyst B was prepared as for catalyst A except that 0.0190 g of tin (II) chloride was additionally added to solution A. The nominal formula of the oxide catalyst obtained was:

$$Mo_{1.000}V_{0.423}Nb_{0.115}Au_{0.0008}Sn_{0.0008}O_y$$

Preparation of Catalyst C

A catalyst C was prepared as for catalyst A except that 0.3792 g of tin (II) chloride was added to solution A. The nominal formula of the oxide catalyst obtained was:

$$Mo_{1.000}V_{0.423}Nb_{0.117}Au_{0.0008}Sn_{0.0156}O_y$$

Preparation of Catalyst D

A catalyst D was prepared as for catalyst A but with addition of 0.0299 g of antimony (III) acetate (FW 298.88) to solution A. The nominal formula of the oxide catalyst was thus:

$$Mo_{1.000}V_{0.423}Nb_{0.115}Au_{0.008}Sb_{0.008}O_y$$

Preparation of Catalyst E

A catalyst E was prepared as for catalyst A but with addition of 0.0200 g of copper (II) acetate (FW 199.65) to solution A. The nominal formula of the oxide catalyst was thus:

$Mo_{1.000}V_{0.423}Nb_{0.115}Au_{0.008}Cu_{0.009}O_y$

Preparation of Catalyst F

A catalyst F was prepared as for catalyst A but with addition of 0.0027 g of platinum acetate (FW 352.66) to solution A. The nominal formula of the oxide catalyst was thus:

$Mo_{1.000}V_{0.423}Nb_{0.115}Au_{0.008}Pt_{0.0006}O_y$

Preparation of Catalyst G

A catalyst G was prepared as for catalyst A but with addition of 0.0174 g of silver (I) acetate (FW 166.92) to solution A. The nominal formula of the oxide catalyst was thus:

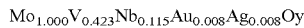
$Mo_{1.000}V_{0.423}Nb_{0.115}Au_{0.008}Ag_{0.008}O_y$

Preparation of Catalyst H

A catalyst H was prepared as for catalyst A but with addition of 0.8080 g of ferric (III) nitrate (FW 404.00) to solution A. The nominal formula of the oxide catalyst was thus:

$Mo_{1.000}V_{0.423}Nb_{0.115}Au_{0.008}Fe_{0.0156}O_y$

Preparation of Catalyst I

A catalyst I was prepared as for catalyst A but with addition of 0.0268 g of ammonium rhenate (FW 268.24) to solution A. The nominal formula of the oxide catalyst was thus:

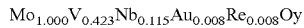
$Mo_{1.000}V_{0.423}Nb_{0.115}Au_{0.008}Re_{0.008}O_y$

Preparation of Catalyst J

A catalyst J was prepared as for catalyst A but with addition of 0.0256 g of gallium nitrate (FW 255.74) to solution A. The nominal formula of the oxide catalyst was thus:

$Mo_{1.000}V_{0.423}Nb_{0.115}Au_{0.008}Ga_{0.008}O_y$

General Ethane Oxidation Reaction Method

Typically 5 ml of a powdered catalyst A to J was mixed with 15 ml of glass beads of diameter 0.4 mm to form a diluted catalyst bed of 20 ml in volume. The diluted catalyst was then loaded into a fixed bed reactor made of Hastelloy of dimensions 12 mm internal diameter and length 40 cm. The catalyst was maintained in position in the centre of the reactor using quartz wall plugs with inert packing material above and below the catalyst bed. The apparatus was than pressure-tested at 20 bar with helium to check for leaks. The catalyst was then activated by heating to 220° C. at 5° C./min in helium at 16 bar for 1 hour, to ensure full decomposition of catalyst precursors.

The required flows of ethane, ethylene, 20% oxygen in helium and water were then introduced to the reactor, to ensure the required inlet composition. This composition was 52% v/v ethane, 6.7% v/v oxygen, 10% v/v ethylene, 5% v/v water and balance helium. The total feed flow rate was maintained at a level to ensure a feed GHSV of 2000-9000/h. After equilibrating for 60 minutes, gas samples were taken from the outlet stream to a GC system (model Unicam 4400) to quantify ethane, ethylene, oxygen and helium.

The setpoint temperature of the reactor was increased to 293° C., to achieve a similar reactor temperature of 299-301° C. for each of catalyst A-J, in order to facilitate direct comparison. Following a further equilibration period of 60 minutes, liquid product collection was commenced and continued for a period of typically 18 hours. During the run period, the effluent gas composition was measured using GC analysis (ProGC, Unicam). Exit gas volume was measured over the run period by a water-gas meter. The liquid products were collected and weighed after the run period. Composition of the liquid products was measured using gas chromatography analysis (Unicam 4400 and 4200 fitted with TCD and FID detectors respectively).

From analysis of the feed and product flow rates and compositions the following parameters were calculated:

Conversions:
of ethane=(inlet mol ethane-outlet mol ethane)/inlet mole ethane*100
of oxygen=(inlet mol oxygen-outlet mol oxygen)/inlet mol oxygen*100

Selectivities:
to acetic acid (C-mol %)=(outlet mol acetic acid*2)/ ((outlet mol ethylene*2−inlet mol ethylene*2)+outlet mol CO+outlet mol $CO_2$+outlet mol acetic acid*2) *100
to ethylene(C-mol %)=(outlet mol ethylene*2)/((outlet mol ethylene*2−inlet mol ethylene*2)+outlet mol CO+outlet mol $CO_2$+outlet mol acetic acid*2)*100
to CO(C-mol %)=(outlet mol CO)/((outlet mole ethylene*2−inlet mol ethylene*2)+outlet mol CO+outlet mol $CO_2$+outlet mol acetic acid*2)*100
to $CO_2$(C-mol %)=(outlet mol $CO_2$)/((outlet mol ethylene*2−inlet mol ethylene*2)+outlet mol CO+outlet mol $CO_2$+outlet mol acetic acid*2)*100
to $CO_x$=selectivity to CO (C-mol %)+selectivity to $CO_2$ (C-mol %)
STY (space time yield) %=(g acetic acid)/kg catalyst bed/hour Typically, mass balance and carbon balance for a reaction was found to be 100+/−5%.

EXPERIMENT A AND EXAMPLES 1 TO 9

Each catalyst A to J was employed in the general reaction method described above. The results are given in Tables 1. Each catalyst was evaluated under standard conditions indicated in Table 1.

TABLE 1

| Experiment | Catalyst | Ethane Convn % C-mol | Sel. Acetic acid % C-mol | Sel. $C_2H_4$ % C-mol | Sel $CO_x$ % C-mol | STY AcOH g/kg-cat/h |
|---|---|---|---|---|---|---|
| A | A | 7.8 | 47.0 | 34.4 | 18.5 | 163 |
| Example 1 | B | 4.2 | 71.3 | 0.0 | 28.7 | 118 |

TABLE 1-continued

| Experiment | Catalyst | Ethane Convn % C-mol | Sel. Acetic acid % C-mol | Sel. C$_2$H$_4$ % C-mol | Sel CO$_x$ % C-mol | STY AcOH g/kg-cat/h |
|---|---|---|---|---|---|---|
| Example 2 | C | 3.8 | 70.8 | 0.0 | 29.2 | 105 |
| Example 3 | D | 6.3 | 56.9 | 24.7 | 18.5 | 133.6 |
| Example 4 | E | 4.1 | 58.4 | 12.9 | 28.7 | 85.9 |
| Example 5 | F | 5.1 | 59.9 | 12.6 | 27.4 | 112.7 |
| Example 6 | G | 3.1 | 63.4 | 1.7 | 34.9 | 99.8 |
| Example 7 | H | 4.7 | 68.1 | 5.6 | 26.4 | 119.3 |
| Example 8 | I | 5.0 | 70.1 | 5.7 | 24.2 | 131.1 |
| Example 9 | J | 5.8 | 53.9 | 27.5 | 18.7 | 115.8 |

Conditions:
52% v/v ethane, 6.7% v/v oxygen, 10% v/v ethylene, 5% v/v water, balance helium.
GHSV = 3200h$^{-1}$; 16 bar The results in Table 1 clearly demonstrates that compared to the comparison catalyst, catalyst A, the catalysts of the present invention achieve higher selectivities to acetic acid. Furthermore, a high selectivity to acetic acid is achieved in combination with reduced selectivity to ethylene.

The invention claimed is:

1. A process for the production of acetic acid from a gaseous mixture comprising ethane and/or ethylene wherein the selectivity to ethylene is less than 25 mol % and which process comprises contacting the gaseous mixture with a molecular oxygen-containing gas at elevated temperature in the presence of a catalyst composition which catalyst composition comprises in combination with oxygen the elements molybdenum, vanadium, niobium, gold in the absence of palladium according to the empirical formula:

$$Mo_aW_bAu_cV_dNb_eZ_f \qquad (I)$$

wherein Z is one or more elements selected from the group consisting of Sn, Sb, Cu, Pt, Ag, Fe and Re;
a, b, c, d, e and f represent the gram atom ratios of the elements such that:
$0 < a \leq 1$; $0 \leq b < 1$ and $a+b=1$;
$10^{-5} < c \leq 0.02$;
$0 < d \leq 2$;
$0 < e \leq 1$; and
$0.0001 \leq f \leq 0.05$.

2. A process as claimed in claim 1 in which ethane or a mixture of ethane and ethylene is oxidized to a mixture comprising acetic acid.

3. A process as claimed in claim 1 in which the elevated temperature is in the range from 200 to 500° C.

4. A process as claimed in claim 1 in which the pressure is the range from 1 to 50 bar.

5. A process as claimed in claim 1 in which the selectivity of the oxidation reaction of ethane and/or ethylene to acetic acid is at least 50 mol %.

6. A process as claimed in claim 5 in which the selectivity of the oxidation reaction of ethane and/or ethylene to acetic acid is at least 60 mol %.

7. A process as claimed in claim 1 in which $0.01 < a \leq 1$, $0.1 < d \leq 2$, $0.01 < e \leq 0.5$ and $0.0005 \leq f \leq 0.02$.

8. A process as claimed in claim 1 in which Z is Sn, Ag, Fe or Re.

9. A process as claimed in claim 1 in which Z is Sn.

10. A process as claimed claim 9 wherein formula I is selected from the group consisting of $Mo_aW_bAu_cV_dNb_eSn_f$ and $Mo_aAu_cV_dNb_eSn_f$.

11. A process as claimed in claim 1 having the formula selected from the group consisting of
$Mo_{1.000}V_{0.423}Nb_{0.115}Au_{0.008}Ag_{0.008}O_y$,
$Mo_{1.000}V_{0.423}Nb_{0.115}Au_{0.008}Fe_{0.0156}Qy$,
$Mo_{1.000}V_{0.423}Nb_{0.115}Au_{0.008}Re_{0.008}O_y$,
$Mo_{1.00}V_{0.423}Nb_{0.115}Au_{0.0008}Sn_{0.0008}O_y$, and
$Mo_{1.00}V_{0.423}Nb_{0.117}Au_{0.0008}Sn_{0.0156}O_y$, wherein y is a number which satisfies the valencies of the elements in the composition for oxygen.

12. A process according to claim 1 in which the selectivity to ethylene is less than 10 mol %.

13. A process according to claim 7 in which the selectivity to ethylene is less than 5 mol %.

* * * * *